United States Patent

Finel et al.

[11] Patent Number: 6,001,339
[45] Date of Patent: *Dec. 14, 1999

[54] HAIR STYLING COMPOSITION

[75] Inventors: Christophe Michel Finel, Compeigne; Deryn Lorraine Nicholls, Upton; Stuart Keith Pratley, West Kirby, all of United Kingdom

[73] Assignee: Helene Curtis, Inc., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/887,998

[22] Filed: Jul. 3, 1997

[30] Foreign Application Priority Data

Jul. 10, 1996 [GB] United Kingdom .................. 9614474

[51] Int. Cl.$^6$ ....................................... A61K 7/06
[52] U.S. Cl. .................... 424/70.12; 424/70.11; 424/70.15; 424/70.19; 424/70.21; 424/70.31; 424/47
[58] Field of Search ............... 424/70.11, 70.12, 424/70.14, 70.122, 70.15, 70.19, 70.21, 70.31, 47

[56] References Cited

U.S. PATENT DOCUMENTS 4,902,499  2/1990  Bolish, Jr. et al. .
5,776,444  6/1998  Birtwistle et al. ................... 424/70.12

FOREIGN PATENT DOCUMENTS

| 0205306 A2 | 12/1986 | European Pat. Off. . |
| 0490582 A1 | 6/1992 | European Pat. Off. . |
| 0523388 A2 | 1/1993 | European Pat. Off. . |
| 06321742 | 12/1987 | Japan . |
| 62281810 | 11/1994 | Japan . |

OTHER PUBLICATIONS

Search Report under Section 17, Application No. GB 96/14474.6 dated Oct. 24, 1996.

*Primary Examiner*—Jyothsna Venkat
*Attorney, Agent, or Firm*—Matthew Boxer

[57] ABSTRACT

The invention provides hair styling compositions in cream, gel or aerosol mousse form comprising:

(i) from 0.1% to 10% by weight, based on total weight, of a non-rigid emulsion polymerised cross-linked silicone polymer, in which the percentage of branched monomer units in the silicone polymer is from 0.05% to 10%; (ii) from 0.1% to 10% by weight, based on total weight, of a hair styling polymer; (iii) from 0.01% to 1% by weight, based on total weight, of a surfactant; (iv) water; and (v) from 0% to 30% by weight, based on total weight, of an aerosol propellant. The compositions impart an excellent balance of styling and conditioning properties to the hair.

1 Claim, No Drawings

6,001,339

HAIR STYLING COMPOSITION

FIELD OF THE INVENTION

The present invention relates to hair styling compositions, for example creams, gels and especially aerosol hair styling mousse compositions, which contain cross-linked silicone and which deliver excellent styling as well as sensory feel.

BACKGROUND AND PRIOR ART

Style creation products such as hair styling mousses provide human hair with a temporary set which can be removed by water or by shampooing, and function by applying a thin film of a resin or gum onto the hair to adhere adjacent hairs together so that they retain the particular shape or configuration at the time of application.

Conventional hair styling mousses typically utilise a hair setting polymer, water, surfactant and propellant gas, with optional adjuvants such as aesthetic agents, fragrance and hair conditioning agents. The conditioning agents used have included silicone-type materials.

EP 0 523 388 discloses an aqueous hair styling aid or mousse composition incorporating a non-volatile silicone compound or other water-insoluble, emulsifiable conditioning agent. The preferred non-volatile silicone compound is a 3:1 mixture of a low molecular weight polydimethylsiloxane fluid and a higher molecular weight polydimethylsiloxane gum.

EP 0 205 306 discloses the use of high molecular weight silicone materials in styling mousses. These are defined as polydiorganosiloxanes having a viscosity of at least 100,000 cSt. The high molecular weight silicone is dissolved in the propellant phase prior to filling the aerosol container.

EP-A-240 350 and U.S. Pat. No. 4,902,499 disclose the use of specific rigid silicone polymers dissolved in a volatile carrier material for giving improved style retention to hair. Silicone elastomers are described which are incorporated in the form of an aqueous silicone emulsion comprising an anionically stabilised hydroxylated polyorganosiloxane, colloidal silica and a catalyst, which crosslinks to form an elastomer on the hair when the water content dries out. Also mentioned are highly cross-linked silicone resins and cross-linked siloxanes which are soluble in solvents such as cyclomethicone.

The present inventors have found that an emulsion polymerised silicone material having a particular, defined level of cross-linking, and which is cross-linked in emulsion form can be incorporated into a hair styling composition, such as a mousse, gel or cream, to give a formulation which delivers excellent style creation and longevity, whilst leaving the hair soft and natural.

Unexpectedly these improved properties have been found to be dependent on the presence of the particular cross-linked silicone and its phase behaviour in the formulated styling composition.

SUMMARY OF THE INVENTION

The present invention provides a hair styling composition comprising:
(i) from 0.1% to 10% by weight, based on total weight, of a non-rigid emulsion polymerised cross-linked silicone polymer, in which the percentage of branched monomer units in the silicone polymer is from 0.05% to 10%;
(ii) from 0.1% to 10% by weight, based on total weight, of a hair styling polymer;
(iii) from 0.01% to 5% by weight, based on total weight, of a surfactant;
(iv) water; and
(v) from 0% to 30% by weight, based on total weight, of an aerosol propellant.

DETAILED DESCRIPTION

Cross-linked Silicone Polymer

The non-rigid emulsion-polymerised cross-linked silicone polymer (i) is present in compositions of the invention in an amount from 0.1% to 10% by weight based on the total weight of the composition, more preferably from 0.2% to 6% by weight, most preferably from 0.5 to 5% by weight.

Preferred silicone polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

The preferred silicone polymers of the invention are cross-linked polydimethyl siloxanes (which have the CTFA designation dimethicone), and cross-linked polydimethyl siloxanes having end groups such as hydroxyl (which have the CTFA designation dimethiconol). Good results have been obtained with cross-linked dimethiconol.

Cross linking of the silicone polymer is typically introduced concurrently during emulsion polymerisation of the polymer through the inclusion of the required amount of trifunctional and tetrafunctional silane monomer units, for example, those of formula:

$R\,Si\,(OH)_3$ wherein R represents an alkyl, alkenyl (e.g. vinyl), alkaryl, aralkyl or aryl (e.g. phenyl) group, preferably methyl.

The degree of cross-linking of the silicone polymer can be measured as the percentage of branched monomer units in the silicone polymer and is from 0.05% to 10%, preferably being in the range 0.15% to 7%, e.g., from 0.2% to 2%. Increasing cross-linking is found to improve styling benefits but also to reduce conditioning performance somewhat, so compromise levels must be selected with properties optimised to suit consumer preferences in different cases. Good overall performance has been obtained with dimethiconol 0.3% cross-linked.

Suitable emulsion polymerised cross-linked silicone polymers are commercially available or can be readily made using conventional techniques well known to those skilled in the art.

Hair Styling Polymer

The hair styling polymer (ii) employed in compositions of the present invention should be capable of forming a film and holding the hair of the user in place.

Hair styling polymers are well known articles of commerce and many such polymers are available commercially which contain functional groups which render the polymers cationic, anionic, amphoteric or nonionic in character.

Examples of cationic hair styling polymers are copolymers of amino-functional acrylate monomers such as lower alkylaminoalkyl acrylate or methacrylate monomers such as dimethylaminoethyl methacrylate with compatible monomers such N-vinylpyrrolidone, vinyl caprolactam, or alkyl methacrylates such as methyl methacrylate and ethyl methacrylate and alkyl acrylates such as ethyl acrylate and n-butyl acrylate. Cationic hair styling polymers containing N-vinylpyrrolidone are commercially available from ISP Corporation such as those sold under the trademarks of Copolymer 845 and Copolymer 937 (copolymers of N-vinylpyrrolidone and t-butylaminoethyl methacrylate of average molecular weight about 1,000,000) and Gafquat® 734, 755 and 755N (quaternary ammonium polymers formed by the reaction of diethyl sulfate and a copolymer of N-vinylpyrrolidone and dimethylaminoethyl methacrylate and having the CTFA designation Polyquaternium-11).

Examples of anionic hair styling polymers are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1:1) wherein such copolymers are 50% esterified with a saturated alcohol containing from 1 to 4 carbon atoms such as ethanol or butanol; and acrylic copolymers, terpolymers, etc., containing acrylic acid or methacrylic acid as the anionic radical-containing moiety and esters of acrylic or methacrylic acid with one or more saturated alcohols having from 1 to 22 carbon atoms such as methyl methacrylate, ethyl acrylate, ethyl acrylate, ethyl methacrylate, n-butyl acrylate, t-butyl acrylate, n-butyl acrylate, t-butyl methacrylate, n-butyl methacrylate, n-hexyl acrylate, n-octyl acrylate, lauryl methacrylate and behenhyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerised terpolymer of methacrylic acid, n-butyl acrylate and ethyl acrylate (e.g., in a weight percent ratio of 31:42:27, respectively). Another specific example is the Gantrez® ES series commercially available from ISP corporation (esterified copolymers of methyl vinyl ether and maleic anhydride).

Examples of amphoteric hair styling polymers are those which contain cationic groups derived from monomers such as t-butyl aminoethyl methacrylate as well as carboxyl groups derived from monomers such as acrylic acid or methacrylic acid. One specific example of an amphoteric hair styling polymer is Amphomer® sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 sold by ISP Corporation under the tradename PVP K-90 and those having an average molecular weight of about 1,000,000 sold under the tradename PVP K-120.

The hair styling polymers in compositions of the invention are most preferably selected from one or more ionic-type, ie cationic and/or anionic, hair styling polymers. Hair styling polymers selected from amphoteric and/or nonionic hair styling polymers may suitably be used in conjunction with these ionic-type hair styling polymers, to improve, for example, hair styling benefit.

Particularly preferred hair styling polymers in compositions of the invention are those ionic-type hair styling polymers selected from Polyquaternium-11, and esterified copolymers of methyl vinyl ether and maleic anhydride, optionally in combination with one or more nonionic hair styling polymers. Such nonionic hair styling polymers are preferably selected from vinylpyrrolidone homopolymers and especially copolymers of vinylpyrrolidone and vinyl acetate.

Surfactant

In addition to the cross-linked silicone polymer and the hair styling polymer, the hair styling composition of the invention also includes a surfactant (iii) in an amount ranging from 0.01% to 5%, preferably from 0.01% to 1%, most preferably from 0.02% to 0.8% by weight based on total weight.

Surfactants are generally classified as nonionic, anionic, cationic, amphoteric or zwitterionic according to their ionic behaviour in aqueous solution.

Examples of nonionic surfactants are condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates.

Examples of anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of cationic surfactants are cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

The surfactants in compositions of the invention are most preferably selected from one or more nonionic surfactants. Surfactants selected from anionic, cationic, amphoteric and zwitterionic surfactants may suitably be used in conjunction with these nonionic surfactants, to improve, for example, foaming power and/or foam stability.

Particularly preferred surfactants in compositions of the invention are those nonionic surfactants selected from polyoxyethylene (9) nonyl phenyl ether, Polysorbate 20, Polysorbate 80 and mixtures thereof, optionally in combination with one or more amphoteric surfactants. Such amphoteric surfactants are preferably selected from lauryl amine oxide, cocodimethyl sulphopropyl betaine, lauryl betaine, sodium cocamphopropionate, and especially cocamidopropyl betaine.

Water

Compositions of the present invention will also include water, preferably distilled or deionised, as a solvent or carrier for the polymers and other components. Water will typically be present in amounts ranging from 30% to 98%, preferably from 60% to 95% by weight based on total weight.

Alcohol may optionally be employed as a co-solvent in compositions of the invention as this can enhance the performance of the styling composition. A suitable alcohol is an aliphatic straight or branched chain monohydric alcohol having 2 to about 4 carbon atoms. Isopropanol and especially ethanol are preferred. A suitable level for the alcohol is up to 20%, preferably from 5% to 15%, by weight based on total weight.

Product Form

Compositions of the invention may suitably be in aerosol form. A particularly preferred product form is an aerosol hair mousse. Aerosol hair mousse compositions are emitted from the aerosol container as a foam which is then typically worked through the hair with fingers or a hair styling tool and either left on the hair or rinsed out.

Aerosol-form compositions of the invention will include an aerosol propellant (v) which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and isobutane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 30%, preferably from 2% to 30%, most preferably from 3% to 15% by weight based on total weight of the composition. If a propellant such as dimethyl ether includes a vapour pressure suppressant (eg trichloroethane or dichloromethane), for weight percentage calculations, the amount of suppressant is included as part of the propellant.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid cross-linked with polyallylsucrose as described in U.S. Pat. No. 2,798,053. These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

Phase Behaviour

Surprisingly, it has been found that the phase behaviour of the cross-linked silicone (i) is important for the performance of the invention.

In, for example, mousse formulations according to the invention, this phase behaviour can be readily observed in vitro, by introducing the mousse formulation into a transparent container, either under standard pressurised conditions of use in the presence of an aerosol propellant, or at ambient pressure, by substituting hexane for the aerosol propellant. On standing, a separate layer forms, which collects at the top of the mixture and can be observed.

The separate layer can be observed to be reversibly dispersible by agitation. Thus, in normal use of the mousse formulation, the separate layer above would be dispersed during agitation of the container by the user, reverting to a separate layer again on standing.

It is believed that this separate layer is a viscous aggregated silicone phase rich in droplets of cross-linked silicone, possibly bound together with the styling polymer, and containing at least 50% water. The mechanism by which this happens, however, is not fully understood.

Without wishing to be bound by any theory, it is believed that the presence of styling polymer and surfactant in the hair styling composition of the invention destabilises the cross-linked silicone, so that the cross-linked silicone tends to aggregate.

In cream or gel formulations according to the invention, the presence of a structurant or thickener as described above prevents the formation af any separate layers in the composition, so the proposed aggregated silicone phase would remain homogeneously dispersed throughout the viscous composition base.

It is theorised, but not relied upon, that the proposed aggregated silicone phase remains intact as small but discrete "lumps" during use of the styling formulations according to the invention. It is believed that these "lumps" serve to bind hair together under low shear, increasing styling power, but are easily dislodged under high shear, improving comb-out. As the hair is dried the water content of the aggregated lumps reduces, eventually leading to dried silicone polymer which due to its high viscosity acts as a highly effective conditioner whilst maintaining style longevity.

The hair styling compositions of the invention can contain a variety of nonessential, optional components suitable for rendering the compositions more aesthetically acceptable or to aid use, including discharge from the container, of the product. Such conventional optional ingredients are well known to those skilled in the art, eg preservatives such as benzyl alcohol, methyl paraben, propyl paraben and imidazolidinyl urea, fatty alcohols such as cetearyl alcohol, cetyl alcohol and stearyl alcohol, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol.

The invention also provides a method of styling hair by applying thereto a styling composition as is hereinabove described.

The following Examples further illustrate the preferred embodiments of the invention. All percentages referred to are by weight unless otherwise indicated.

EXAMPLES

The following Examples 1 and 2 illustrate hair styling compositions according to the invention.

Example 1

| % active ingredient | Trade Name | Chemical Name |
| --- | --- | --- |
| 1.0% | Gafquat 734 | Polyquaternium-11 |
| 1.0% | Gafquat 755N | Polyquaternium-11 (high molecular weight) |
| 8% | EtOH B Denatured | Ethanol |
| 2.0% | | Cross-linked silicone* |
| 0.02% | BHT | Butylated hydroxy toluene |
| 0.01% | Bronopol | 2-bromo-2-nitropropane-1,3-diol |
| 0.3% | Empilan NP9 | Polyethyleneglycol (9) nonyl phenyl ether |
| 15.0% | CAP30 | Propane/butane |
| 0.1% | Triance 633 | Perfume |
| 0.02% | EDTA | Ethylene diamine tetra acetic acid |
| to 100% | | deionised water |

*Emulsion polymerised dimethiconol containing 0.6% cross-linking, 55% aqueous emulsion, ex Dow Corning.

Example 2

| % active ingredient | Trade Name | Chemical Name |
| --- | --- | --- |
| 0.5% | Gafquat 734 | Polyquaternium-11 |
| 0.5% | Gafquat 755N | Polyquaternium-11 (high molecular weight) |
| 8% | EtOH B Denatured | Ethanol |
| 1.0% | | Cross-linked silicone* |
| 0.02% | BHT | Butylated hydroxy toluene |
| 0.01% | Bronopol | 2-bromo-2-nitropropane-1,3-diol |
| 0.3% | Empilan NP9 | Polyethyleneglycol (9) nonyl phenyl ether |
| 15.0% | CAP30 | Propane/butane |
| 0.1% | Triance 633 | Perfume |
| 0.02% | EDTA | Ethylene diamine tetra acetic acid |
| to 100% | | deionised water |

*as Example 1

The sensory properties of the formulations of Examples 1 and 2 were evaluated in comparison with a control formulation having the following ingredients:

Control Formulation

| % active ingredient | Trade Name | Chemical Name |
| --- | --- | --- |
| 4.5% | PVP/VA | Poly vinyl pyrrolidone /vinyl acetate copolymer |
| 5% | EtOH B Denatured | Ethanol |
| 0.02% | BHT | Butylated hydroxy toluene |
| 0.01% | Bronopol | 2-bromo-2-nitropropane-1,3-diol |
| 0.3% | Empilan NP9 | Polyethyleneglycol (9) nonyl phenyl ether |
| 5.0% | CAP30 | Propane/butane |
| 0.1% | Triance 633 | Perfume |
| 0.02% | EDTA | Ethylene diamine tetra acetic acid |
| 0.08% | Arquad 16/50 | Cetyl trimethyl ammonium chloride |
| 1.25% | Luviquat FC 550 | Polyquaternium-16 |
| to 100% | | deionised water |

The formulations of Examples 1 and 2 and the control formulation were subjected to a panellist evaluation for the descriptors unnatural feel, initial curl definition, hold and quality of style. The following Table gives the average scores, on a scale of 0–10, attributed to each formulation by the panellists (average 20 panellists per test).

| Descriptor | Ex 1 | Ex 2 | Control |
| --- | --- | --- | --- |
| Unnatural feel | 3.2 | 2.6 | 5.3 |
| Initial curl definition | 7.8 | 7.2 | 7.2 |
| Hold | 6.7 | 6.7 | 6.1 |
| Quality of Style | 7.0 | 6.9 | 5.9 |

A further formulation (Comparative Example A) was prepared having the following ingredients:

Comparative Example A

| % active ingredient | Trade Name | Chemical Name |
| --- | --- | --- |
| 1.5% | Gafquat 755N | Polyquaternium-11 (high molecular weight) |

-continued

| % active ingredient | Trade Name | Chemical Name |
|---|---|---|
| 8% | EtOH B Denatured | Ethanol |
| 2.0% | DC244 | Cyclomethicone |
| 0.02% | BHT | Butylated hydroxy toluene |
| 0.01% | Bronopol | 2-bromo-2-nitropropane-1, 3-diol |
| 0.3% | Empilan NP9 | Polyethyleneglycol (9) nonyl phenyl ether |
| 8.0% | CAP30 | Propane/butane |
| 0.1% | Triance 633 | Perfume |
| 0.02% | EDTA | Ethylene diamine tetra acetic acid |
| to 100% | deionised water | |

Comparative Example A was assessed against the control formulation for styling attributes by a panellist evaluation for the descriptors initial curl definition, hold and quality of style. The following Table gives the average scores, on a scale of 0–100, attributed to each formulation by the panellists (average 20 panellists per test).

| Descriptor | CompEx.A | Control |
|---|---|---|
| Initial curl definition | 50 | 62 |
| Hold | 65 | 72 |
| Quality of Style | 48 | 67 |

The results illustrate that for the Examples of the invention, styling power is equivalent or superior to that of the silicone-free control yet unnatural feel is reduced.

Addition of a standard silicone such as cyclomethicone, however (Comparative Example A) adversely affects style benefits compared with the silicone-free control.

Phase Behaviour

Examples 3 to 5 and Comparative Examples B, C and D

To demonstrate the importance of phase behaviour to the improved performance of compositions of the invention, six formulations were prepared with ingredients as shown below:

Example 3

| % active ingredient | Trade Name | Chemical Name |
|---|---|---|
| 1.0% | Gafquat 734 | Polyquaternium-11 |
| 8% | EtOH B Denatured | Ethanol |
| 1.0% | | Cross-linked silicone* |
| 0.3% | Empilan NP9 | Polyethyleneglycol (9) nonyl phenyl ether |
| 15.0% | Hexane | |
| to 100% | deionised water | |

*as for Example 1

Example 4

| % active ingredient | Trade Name | Chemical Name |
|---|---|---|
| 1.0% | Gafquat 734 | Polyquaternium-11 |
| 8% | EtOH B Denatured | Ethanol |
| 1.0% | | Cross-linked silicone* |
| 0.3% | Tween 80 | Polysorbate 80 |
| 15.0% | Hexane | |
| to 100% | deionised water | |

*as for Example 1

Comparative Example B

| % active ingredient | Trade Name | Chemical Name |
|---|---|---|
| 1.0% | Gafquat 734 | Polyquaternium-11 |
| 8% | EtOH B Denatured | Ethanol |
| 1.0% | | Cross-linked silicone* |
| 0.3% | CAPB | Cocoamidopropylbetaine |
| 15.0% | Hexane | |
| to 100% | deionised water | |

*as for Example 1

Comparative Example C

| % active ingredient | Trade Name | Chemical Name |
|---|---|---|
| 1.0% | Gafquat 734 | Polyquaternium-11 |
| 8% | EtOH B Denatured | Ethanol |
| 1.0% | | Cross-linked silicone* |
| 0.3% | Synperonic A11 | Trideceth-11 |
| 15.0% | Hexane | |
| to 100% | deionised water | |

*as for Example 1

Comparative Example D

| % active ingredient | Trade Name | Chemical Name |
|---|---|---|
| 1.0% | PVP/VA | Poly vinyl pyrrolidone vinyl acetate copolymer |
| 8% | EtOH B Denatured | Ethanol |
| 1.0% | | Cross-linked silicone* |
| 0.3% | Empilan NP9 | Polyethyleneglycol (9) nonyl phenyl ether |
| 15.0% | Hexane | |
| to 100% | deionised water | |

*as for Example 1

Example 5

| % active ingredient | Trade Name | Chemical Name |
| --- | --- | --- |
| 1.0% | Gantrez ES425 | n-Butyl ester of PVM/MA copolymer |
| 0.4% | AMP | Amino Methyl Propanol |
| 8% | EtOH B Denatured | Ethanol |
| 1.0% | | Cross-linked silicone* |
| 0.3% | Empilan NP9 | Polyethyleneglycol (9) nonyl phenyl ether |
| 15.0% | Hexane | |
| to 100% | deionised water | |

*as for Example 1

Results

Examples 3, 4 and 5 separated within 3 hrs to give two distinct layers, with the opaque upper layer being less than half the volume. When used by stylers on both curly switches and straight hair wigs, they could be easily styled and the style stayed in place longer compared with Comparative Examples B, C and D which did not separate within 3 hrs.

Comparative Example E

The following formulation was prepared:

| % active ingredient | Trade Name | Chemical Name |
| --- | --- | --- |
| 3.0 | Yukaformer SM | Carboxybetaine methacrylate copolymer |
| 0.3 | Amphomer 28-4910 | Octylacrylamide/Acrylates Butylaminoethyl/ Methacrylate copolymer |
| 0.05 | AMP | Amino methyl propinol |
| 1.2 | KM889 | Methyl polysiloxane |
| 0.5 | KF-995 | Decamethyl cyclopentasiloxane |
| 0.4 | SH 3771C | Dimethicone copolyol |
| 0.1 | SH 3772C | Dimethicone copolyol |
| 2.0 | Malbit | Maltitol |
| 5.0 | | EtOH |
| 0.1 | | Perfume |
| 0.45 | Liponocks NC-95 | Nonylphenolether |
| 7.0 | L.P.G | Propane/Butane |

Example 6

The following formulation was prepared:

| % active ingredient | Trade Name | Chemical Name |
| --- | --- | --- |
| 4.0 | | Cross-linked silicone* |
| 1.5 | Gafquat 734 | Polyquaternium 11 |
| 1.5 | Luviskol VA 64E | PVP/VA copolymer |
| 0.4 | Tween 20 | Polysorbate 20 |
| 8 | | EtOH |
| 0.1 | | Perfume |
| 8 | L.P.G | Propane/Butane |

*as for Example 1

The formulations of Example 6 and Comparative Example E were subjected to a panellist evaluation for the descriptors hair not stiff, hair made moisturised and defined hair curl. The following Table gives the average scores, on a scale of 0–5, attributed to each formulation by the panellists (average 100 panellists per test)

| Descriptor | CompEx.E | Example 6 |
| --- | --- | --- |
| Hair not stiff | 3.84 | 4.85 |
| made moisturised | 3.88 | 4.40 |
| defined hair curl | 4.64 | 4.33 |
| reduced hair volume | 4.58 | 4.45 |
| desired style achieved | 4.39 | 4.45 |

The results illustrate that for the Example of the invention containing cross-linked silicone, the conditioning attributes of reduced stiffness and moisturisation are superior to the Comparative Example containing non-cross-linked silicone, yet there is less perception of reduced hair volume, and improvement in desired style achieved. This indicates an overall optimised balance of styling and conditioning for the Example of the invention.

Example 7

The following formulation was prepared:

| % active ingredient | Trade Name | Chemical Name |
| --- | --- | --- |
| 2.0 | | Cross-linked silicone* |
| 0.75 | Gafquat 734 | Polyquaternium 11 |
| 0.75 | Gafquat 755N | Polyquaternium 11 |
| 0.2 | Tween 80 | Polysorbate 20 |
| 0.2 | CAPB | Cocoamidopropyl betaine |
| 8 | | EtOH |
| 0.1 | | Perfume |
| 8 | L.P.G | Propane/Butane |

*as for Example 1

Comparative Example F

The following formulation was prepared:

| % active ingredient | Trade Name | Chemical Name |
| --- | --- | --- |
| 2.0 | DC X2-1784 | High molecular weight polysiloxane |
| 0.75 | Gafquat 734 | Polyquaternium 11 |
| 0.75 | Gafquat 755N | Polyquaternium 11 |
| 0.4 | Tween 80 | Polysorbate 20 |
| 8 | | EtOH |
| 0.1 | | Perfume |
| 8 | L.P.G | Propane/Butane |

The formulations of Example 7 and Comparative Example F were subjected to a panellist evaluation for the descriptors easy wet comb, hair difficult to style and hair unnatural feel.

The following Table gives the average scores, on a scale of 0–10, attributed to each formulation by the panellists (average 20 panellists per test)

| Attribute | Example 7 | Comp.Ex.F |
|---|---|---|
| Easy wet comb | 7.8 | 7.3 |
| difficult to style | 3.1 | 3.9 |
| hair has unnatural feel | 2.8 | 2.7 |

The results illustrate that for the Example of the invention containing cross-linked silicone, the conditioning attribute of easy wet comb is superior to the Comparative Example containing non-cross-linked high molecular weight polysiloxane, which is recognised as a highly effective conditioner. However there is improved ease of styling with the Example of the invention, with only a marginal increase in unnatural feel, again indicating an overall optimised balance of styling and conditioning for the Example of the invention.

We claim:

1. A hair styling composition comprising:
(i) from 0.15% to 7% based on total weight of a non-rigid emulsion polymerized crosslinked silicone polymer which is dimethiconol;
(ii) Polyquaternium-11 from 0.1 to 10% by weight;
(iii) from 0.01% to 1% by weight based on total weight of a surfactant selected from the group consisting of polyoxyethylene (9) nonyl phenyl ether, Polysorbate 20, Polysorbate 80 in combination with one or more amphoteric surfactants selected from the group consisting of lauryl amine oxide, cocodimethylsulphopropyl betaine, lauryl betaine, sodium cocamphopropionate, cocamidopropyl betaine, and mixtures thereof;
(iv) from 5% to 15% by weight an alcohol selected from the group consisting of straight or branched chain monohydric alcohols having 2 to 4 carbon atoms; and
(v) 2% to 30% by weight a propellant selected from the group consisting of propane, n-butane, isobutane and mixtures thereof.

* * * * *